United States Patent [19]

Hübenett

[11] 4,280,966
[45] Jul. 28, 1981

[54] PROCESS FOR THE PREPARATION OF ALKANESULFONYL CHLORIDES

[75] Inventor: Fritz Hübenett, Darmstadt, Fed. Rep. of Germany

[73] Assignee: Merck Patent Gesellschaft mit beschränkter Haftung, Darmstadt, Fed. Rep. of Germany

[21] Appl. No.: 86,507

[22] Filed: Oct. 19, 1979

[30] Foreign Application Priority Data

Oct. 21, 1978 [DE] Fed. Rep. of Germany ....... 2845918

[51] Int. Cl.³ .......................... C07C 43/70; C01B 7/07
[52] U.S. Cl. .................................. 260/543 R; 423/488
[58] Field of Search ...................... 260/543 R; 423/488

[56] References Cited

U.S. PATENT DOCUMENTS

| 2,598,014 | 5/1952 | Proell | 260/543 R |
| 3,600,136 | 8/1971 | Giolito | 260/543 R |
| 3,626,004 | 12/1971 | Guertin | 260/543 R |
| 3,993,629 | 11/1976 | Giolito | 260/543 R |

Primary Examiner—Howard T. Mars
Assistant Examiner—Michael Shippen
Attorney, Agent, or Firm—Millen & White

[57] ABSTRACT

A process is provided for preparing alkanesulfonyl chlorides having 1–12 carbon atoms, in which the reaction of the corresponding alkanethiols and/or dialkyl disulfides with chlorine and water at a temperature of between −10 ® and +50° C. is carried out in the desired alkanesulfonyl chloride as the reaction medium. The reaction can be carried out batchwise or continuously in a circulatory reactor, mixing of the reactants being effected by the hydrogen chloride formed in the reaction.

9 Claims, 1 Drawing Figure

PROCESS FOR THE PREPARATION OF ALKANESULFONYL CHLORIDES

BACKGROUND OF THE INVENTION

The invention relates to a process for preparing alkanesulfonyl chlorides by reacting alkanethiols and/or dialkyl disulfides with chlorine and water.

Alkanesulfonyl chlorides having 1-12 carbon atoms are used in large quantities as starting materials and intermediates for organic syntheses, for example of plant protection agents or photographic color developers. Various processes for their preparation, including preparation on an industrial scale, are known, and amongst these the synthesis from alkanethiols or dialkyl disulfides by reaction with chlorine and water is preferred. The disadvantages of this known, batchwise process are the as yet unsatisfactory yields, a purity of the reaction products which is insufficient for many applications, and the need to use mechanical stirring equipment.

In addition, a process for the continuous preparation of alkanesulfonyl chlorides, in which alkanethiols or dialkyl disulfides, in concentrated aqueous hydrochloric acid, are reacted with chlorine in a circulatory reactor, is known from German Offenlegungsschrift No. 1,811,768. The requisite intensive mixing of the reactants is in that case effected by the hydrogen chloride formed during the reaction. The alkanesulfonyl chloride, which is of greater specific gravity, separates out from the aqueous hydrochloric acid serving as the reaction medium as soon as the latter has become saturated therewith at the reaction temperature. To permit sufficiently rapid separating-out, a part of the hydrochloric acid saturated with the alkanesulfonyl chloride must be drawn off intermittently or continuously and replaced by water or fresh hydrochloric acid. Herein resides a substantial disadvantage of this known process, since some dissolved alkanesulfonyl chloride is drawn off with the hydrochloric acid and can only be isolated therefrom by an expensive work-up. In the preparation of methanesulfonyl chloride, about 10 percent by weight of the reaction medium drawn off is methanesulfonyl chloride. If such isolation is dispensed with, the yield, and hence also the economy of the process, is diminished. Furthermore, increased effort is then needed for detoxification, in the interest of protecting the environment.

OBJECTS OF THE INVENTION

It is therefore an object of the invention to develop a process for the preparation of alkanesulfonyl chlorides, in which this product can easily be substantially completely recovered from the reaction mixture.

Upon further study of the specification and appended claims, further objects and advantages of this invention will become apparent to those skilled in the art.

SUMMARY OF THE INVENTION

According to the invention, these objects are achieved, in a process for the preparation of alkanesulfonyl chlorides having 1-12 carbon atoms by reaction of the corresponding alkanethiols and/or dialkyl disulfides with chlorine and water at a temperature of between $-10°$ and $+50°$ C., by the improvement wherein the desired alkanesulfonyl chloride serves as the reaction medium.

DETAILED DISCUSSION

Figure 1:
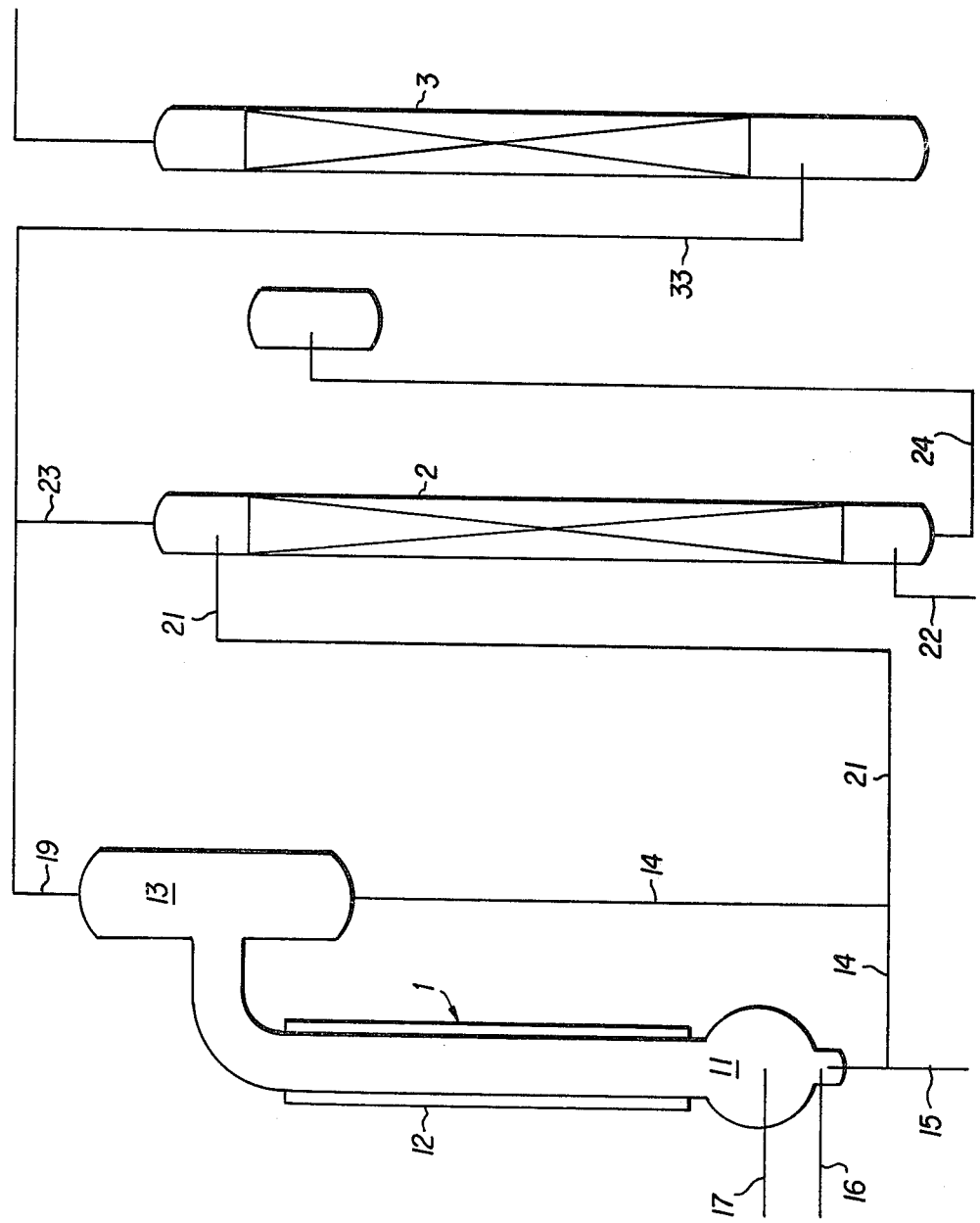
FIG. 1 is a schematic diagram of an apparatus for effecting a continuous process according to the invention.

The reaction which takes place in the process according to the invention can be represented by the following equations:

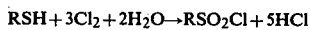

or

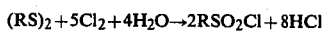

wherein R denotes an alkyl group having 1-12 carbon atoms. Suitable such alkyl groups include any straight or branched chain saturated $C_{1-12}$ alkyl residue; e.g., methyl, ethyl, propyl, isopropyl, n-butyl, isobutyl, sec-butyl, tert-butyl, n-hexyl, isooctyl, 2-ethylhexyl, 3,8-dimethyloctyl, n-dodecyl, and the like.

The process according to the invention can be carried out batchwise in any conventional reaction apparatus. However, it is advantageous to effect the reaction continuously in a continuously operated circulatory apparatus. Usually, the reaction is carried out substantially at atmospheric pressure, while either atmospheric pressure or reduced pressure may be used in the purification steps. The reaction temperature is between $-10°$ and $50°$ C., preferably between $25°$ and $35°$ C. Both in batchwise and in continuous operation, the preferred temperature range can be easily obtained by simple water cooling; the process can thus be controlled with minimum possible expense. On the other hand, higher reaction temperatures, for example of $40°-50°$ C., are advantageous when preparing alkanesulfonyl chlorides which are solid at room temperatures.

Starting materials used are alkanethiols, dialkyl disulfides in which the two alkyl groups are identical, or mixtures thereof. As a rule, dialkyl disulfides are preferred as starting materials for the preparation of the lower alkanesulfonyl chlorides and alkanethiols as starting materials for the preparation of the higher derivatives. Of course, the lower alkanesulfonyl chlorides can also be prepared from the alkanethiols.

Chlorine may be introduced as a gas or a liquid. If liquid chlorine is available, its introduction in this form is advantageous in the case of fairly large installations because a part of the heat of reaction is removed as heat of vaporization, so that less cooling is necessary.

The reactants are as a rule separately fed into the reaction system. In principle, however, it is also possible to employ the alkanethiol or the dialkyl disulfide in the form of an emulsion with water. To prepare such an emulsion, conventional surface-active agents, in very low concentrations, may also be added as emulsifiers.

As a rule, the reactants are employed in substantially stoichiometric or at least approximately stoichiometric amounts. It has proved advantageous to use a slight excess of chlorine over the stoichiometric amount, the excess being, e.g., from 0.1 to 5 percent, preferably from 0.1 to 2 percent more than the stoichiometric amount of chlorine. By doing so, traces of sulfur compounds, which can become entrained by the vigorous evolution of gas, are oxidized in the downstream, adiabatically-operated absorption column. As a result, after neutralization of the hydrochloric acid obtained as a by-product, foul-smelling sulfur compounds of low degrees of oxidation are not detectable therein.

Preferably, not more than the stoichiometric amount of water is used. Thus, the present process differs from that disclosed in the aforementioned German Offenlegungsschrift in that the prior art process uses an excess of water, in the form of aqueous hydrochloric acid, to effect the reaction. In addition, some product alkanesulfonyl chloride produced in the prior art process is either lost or difficult and costly to recover from the hydrochloric acid medium.

The process according to the invention offers particular advantages if it is carried out continuously in a conventional circulatory reactor, wherein the mixing of the reactants is effected by the hydrogen chloride generated during the reaction. A preferred embodiment of an apparatus in which the process according to the invention can be carried out is shown in FIG. 1. The apparatus consists of a circulatory reactor (1) and a purification device (2) for the alkanesulfonyl chloride produced; it has proved advantageous additionally to provide an absorption system (3) for the hydrogen chloride formed during the reaction.

The circulatory reactor (1) consists of a reaction zone (11), a cooler (12), a gas separator (13) and a circulation line (14). Feed lines for chlorine (15), for alkanethiol or dialkyl disulfide (16), and for water (17) enter the reaction zone (11). The arrangement of the feed lines shown in the drawing has proved particularly advantageous for carrying out the process according to the invention on an industrial scale because in this way losses of unconverted alkanethiol or dialkyl disulfide are kept particularly low. In principle, however, it is also possible, for example, to use feed line (15) for alkanethiol or dialkyl disulfide and feed line (16) for chlorine, or to have all three feed lines (15), (16) and (17) enter the reaction zone (11) adjacent to one another.

The cooler (12) can in principle be of any desired construction; it is merely necessary for it to be of such size that the heat of reaction can be removed. The use of a tubular cooler has proved particularly advantageous. The gas separator (13), in which the reaction products, namely alkanesulfonyl chloride and hydrogen chloride, are separated, can again be of any conventional type. Cyclone or baffle separators are used preferentially.

A portion of the alkanesulfonyl chloride separated off flows through the circulation line (14) back into the reaction zone (11), and a portion flows through the discharge line (21) into the purification device (2). This purification device (2) can be, for example, a bubble column, in which air or an inert gas, such as nitrogen, is fed through feed line (22) counter-currently to the alkanesulfonyl chloride in order to expel the hydrogen chloride dissolved in the product. Instead of a bubble column, a trickle column operated under reduced pressure, or a kettle for vacuum degassing, may also, for example, be used as the purification device (2). The alkanesulfonyl chloride purified in this way is fed to the end product container through the discharge line (24). The off-gas of the bubble column is fed, through the line (23)/(33), together with the hydrogen chloride escaping from the gas separator through the discharge line (19)/(33), to the absorption system (3). The absorption system (3) is of generally conventional construction, and its efficiency essentially depends on the standards to be met in the interest of protecting the environment.

To carry out the present process continuously, the circulatory reactor (1) is charged with an amount of the alkanesulfonyl chloride to be prepared such that after the subsequent introduction of chlorine, alkanethiol or dialkyl disulfide and water, and hence after commencement of the formation of the alkanesulfonyl chloride, the circulation is set up immediately. The relevant feed lines are advantageously opened in the abovementioned sequence in order to obtain as near to the very beginning as possible an off-gas which is free from volatile and foul-smelling sulfur compounds.

Using the process according to the invention, alkanesulfonyl chlorides having 1–12 carbon atoms are obtained in very high purity, that is, with substantially less than 1% of impurities, and in excellent yields, generally at least 95% and preferably at least 98%. The aforementioned advantages of the present process are most apparent in the preparation of alkanesulfonyl chlorides which are liquid at room temperature, especially the preparation of methanesulfonyl chloride.

Surprisingly, the gaseous effluent from the process according to the invention consists, in addition to air or inert gas blown in during the purification process, of hydrogen chloride which is so pure that it can be used, in the absorption device, for the preparation of very pure aqueous hydrochloric acid. This hydrochloric acid contains less than 0.2% of impurities and can be obtained in a strength of from 28 to 34% by weight, preferably from 30 to 32%. If the process according to the invention is additionally carried out with a slight excess of chlorine, sulfur compounds are not detectable, even by odor, after neutralizing the hydrochloric acid formed as a by-product. Recovery of hydrogen chloride is generally high, e.g., at least 90% and preferably at least 95% of theory.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

EXAMPLE 1

3,504 g of methanesulfonyl chloride are introduced into an apparatus corresponding to FIG. 1. In the course of 24 hours, 3,956 g (42 moles) of dimethyl disulfide in the form of an emulsion in 3,026 g (168 moles) of water, produced using 21 ml of a commercial nonylphenol polyglycol ether, are fed in, and 15.19 kg (214 moles) of chlorine gas are blown in at a rate of 220–240 liters per hour. A bubble column filled with Raschig rings serves as the purification device (2). Air is introduced into the column through line (22) to expel dissolved HCl from the methanesulfonyl chloride formed. Cooling takes place by means of a high-efficiency cooler; the reaction temperature is 29° C.

In 24 hours, 9,531 g of methanesulfonyl chloride (99% of theory), of 99.6% purity as determined by gas chromatography, are drawn off, not counting the amount of methanesulfonyl chloride initially introduced as the reaction medium. During this time, 39.2 kg of a very pure aqueous 30.3% strength hydrochloric acid (97% of theory) are obtained from the absorption system (3). The impurities present in the hydrochloric acid are only 0.2% of methanesulfonic acid, <1 ppm of free chlorine and <5 ppm of sulfate ions.

EXAMPLE 2

2,460 g of dodecanesulfonyl chloride, warmed to 50° C., are introduced into an apparatus analogous to Example 1, and to prevent crystallization the circulation line (14) and the bubble column (2) are also kept at 50° C., by means of heater bands. In the course of 5 hours, 1,518 g (7.5 moles) of dodecylmercaptan, in the form of an emulsion with 270 g (15 moles) of water (emulsifier: 2 ml of a commercial nonylphenol polyglycol ether) are fed in. At the same time, 115 liters of chlorine gas per hour are introduced. 1,976 g of dodecanesulfonyl chloride (m.p. 42° C.; 98% of theory) and 4.2 kg of an aqueous 31.5% strength hydrochloric acid are obtained.

EXAMPLE 3

Per hour, 13.65 liters of dimethyl disulfide, 11.0 liters of water and 55.4 kg of liquid chlorine are fed into an apparatus, built from industrial glass and provided with a cooler (12), a bubble column (2) 3.0 meters in length, and an HCl absorption column (3) 4.0 meters in length. The reaction temperature is kept at 30° C. 34.8 kg per hour of methanesulfonyl chloride (99.2% of theory) are drawn off through the discharge line (24); according to analysis by gas chromatography, this material is 99.4% pure. At the same time, 38.1 kg per hour of an aqueous 30.8% strength hydrochloric acid of very high purity are obtained from the absorption column. The impurities contained in the hydrochloric acid are only 0.1% of methanesulfonic acid and 2 ppm of free chlorine.

It can be seen from the examples that the yields of both alkanesulfonyl chloride and hydrochloric acid and the purity of the products are high, when the process of the invention is carried out as hereinbefore described.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for preparing an alkanesulfonyl chloride having 1-12 carbon atoms by reacting at least one of the corresponding alkanethiol and dialkyl disulfide with chlorine and water at a temperature of from −10 to +50° C.; the improvement which comprises using said alkanesulfonyl chloride as the reaction medium and effecting the reaction with not more than the stoichiometric amount of water.

2. The process of claim 1 wherein the reaction is carried out continuously in a circulatory reactor, mixing of the reactants being effected by the hydrogen chloride formed in the reaction.

3. The process of claim 1, wherein the reaction temperature is from 25° to 35° C.

4. The process of claim 1, wherein the reaction is effected with an excess of chlorine over the stoichiometric amount, said excess being from 0.1 to 5 percent more than the stoichiometric amount.

5. The process of claim 1, wherein dimethyl disulfide is reacted to form methanesulfonyl chloride in a continuous process effected in a circulatory reactor, mixing of the reactants being effected by the hydrogen chloride formed in the reaction.

6. The process of claim 5, wherein the reaction temperature is from 25° to 35° C.

7. The process of claim 6, wherein the reaction is effected with an excess of chlorine over the stoichiometric amount, said excess being from 0.1 to 5 percent more than the stoichiometric amount.

8. The process of claim 1, wherein the hydrogen chloride produced in the reaction is absorbed in water and recovered as an aqueous hydrochloric acid solution.

9. The process of claim 1, wherein dimethyl disulfide is reacted to form methanesulfonyl chloride.

* * * * *